United States Patent [19]

Horiuchi

[11] Patent Number: 4,634,663

[45] Date of Patent: Jan. 6, 1987

[54] METHOD AND REAGENT FOR QUANTITATIVE DETERMINATION OF N-ACETYLHEXOSAMINE

[75] Inventor: Tatsuo Horiuchi, Noda, Japan

[73] Assignee: Noda Institute for Scientific Research, Japan

[21] Appl. No.: 580,246

[22] Filed: Feb. 15, 1984

[30] Foreign Application Priority Data

Feb. 28, 1983 [JP] Japan .................................. 58-30802

[51] Int. Cl.⁴ .......................... C12Q 1/26; C12Q 1/00; C12Q 1/28; C12Q 1/34
[52] U.S. Cl. .......................................... 435/25; 435/4; 435/28; 435/18; 435/810
[58] Field of Search .................... 435/4, 15, 18, 21, 25, 435/28, 189, 190, 191, 192, 810, 874

[56] References Cited

PUBLICATIONS

Chemical Abstracts, 101: 226338g, 405 (1984).
Chemical Abstracts, 102: 60787w, 481 (1985).

Primary Examiner—Esther M. Kepplinger
Attorney, Agent, or Firm—Banner, Birch, McKie & Beckett

[57] ABSTRACT

A method for quantitative determination of N-acetylhexosamine which comprises (a) allowing an N-acetylhexosamine oxidase to act upon an N-acetylhexosamine-containing liquid in the presence of oxygen and then (b) determining the amount of oxygen consumed in the oxidation reaction or the amount of hydrogen peroxide or N-acetylhexaminic acid formed in the oxidation reaction. Further, a reagent for quantitative determination of N-acetylhexosamine, characterized by containing an N-acetylhexosamine oxidase.

4 Claims, 5 Drawing Figures

METHOD AND REAGENT FOR QUANTITATIVE DETERMINATION OF N-ACETYLHEXOSAMINE

This invention relates to a novel method for quantitative determination of N-acetylhexosamine by the use of an N-acetylhexosamine oxidase as well as to a reagent used in the method.

In living bodies, N-acetylhexosamine rarely exists as it is and generally exists as a constituent of complex glycides present at outermost layers of cells or of mucopolysaccharides present among cells.

It has been made clear recently that, in cancerous cells, as one of their characteristics, there occurs an information lack among cells (lack of contact inhibition). It has been also clarified that the carrier of the above information is complex glycides present at outermost layers of cells. Accordingly, it has been pointed out that canceration is modification of complex glycides which causes change of activities of enzymes related to metabolism of amino sugars in living bodies. It has also become clear that canceration invites abnormal metabolism of mucopolysaccharides and complex saccharides which brings about urinary eccrisis and "within tissue" accumulation of mucopolysaccharides and oligosaccharides. Thus, determination of amino sugar-related enzymes and/or identification of amino sugar-containing saccharides provides an important means in inspection or grasping of conditions of diseases. Hence, an superior method for quantitative determination of amino sugars has been desired.

As methods for quantitative determination of N-acetylhexosamine, there are currently available the Morgan-Elson method, the Levvy-McAllan method, etc. However, all these methods conduct color development under severe conditions and hence working machine and the operator's damages are big. Further, buffer solutions, amino acids and proteins used or co-existing in determination are liable to affect badly and therefore the above methods are insufficient in sensitivity, stability, etc. On the other hand, when a quantitative determination of mild conditions and having a high specificity is required, there can be used methods utilizing unique reactions by enzymes, for example, a method using N-acetylglucosamine kinase. However, in this method, influences of enzymes and reaction intermediates present in the samples as living body fluid and are unavoidable and moreover coupled enzymatic reactions which are complex must be used. Accordingly, a method enabling a direct determination of N-acetylhexosamine has been particularly desired in the art.

In light of the above situation, the present inventor has made extensive studies in order to establish a method for quantitatively determining N-acetylhexosamine rapidly and accurately. As a result, the present invention has been completed.

An object of the present invention is to provide a method for quantitative determination of N-acetylhexosamine.

Another object of the present invention is to provide a reagent for quantitative determination of N-acetylhexosamine.

Other objects and advantages of the present invention will be made clear by the following description.

According to the present invention, there is provided a method for quantiative determination of N-acetylhexosamine which comprises (a) allowing an N-acetylhexosamine oxidase to act upon an N-acetylhexosamine-containing liquid in the presence of oxygen and then (b) determining the amount of oxygen consumed in the oxidation reaction or the amount of hydrogen peroxide or N-acetylhexosaminic acid formed in the oxidation reaction.

According to the present invention, there is also provided a reagent for quantitative determination of N-acetylhexosamine, characterized by containing an N-acetylhexosamine oxidase.

In the accompanying drawings.

The quantitative determination method of the present invention is based on the following reaction.

As the N-acetylhexosamine oxidase, particularly N-acetylhexosamine oxidase has a high applicability.

As the test liquid used in the quantitative determination of the present invention, any liquid containing N-acetylhexosamine can be used. Such liquids include, for example, a liquid obtained by separating acidic mucopolysaccharides from human urine, decomposing them with hydrochloric acid and then acetylating the decomposed mucopolysaccharides, a liquid obtained by decomposing chitin with chitinase and chitobiase, a liquid obtained by decomposing hexa-N-acetyl-chitohexaose with lysozyme and N-acetylhexosaminidase, and liquids formed by action of various hexosamine synthesis enzymes.

As the N-acetylhexosamine oxidase used in the quantitative determination method of the present invention, those of any origin can be used, however, it is preferable to use, for example, an N-acetylhexosamine oxidase obtained by culturing microorganisms, particularly a bacterium selected from bacteria belonging to the genus Pseudomonas. As the bacterium belonging to the genus Pseudomonas and producing the above enzyme, there can be mentioned, for example, Pseudomonas sp. No. 15-1. This Pseudomonas sp. No. 15-1 is a new bacterial strain separated from a soil by the present inventor and has the following properties.

(A) Form

Microscopic observation after culture in a bouillon-agar medium for 16 hr at 30° C.

(1) Cell size: A bacillus having a cell size of 0.5 to 0.8 micron by 1.0 to 1.3 micron.
(2) Polymorphism of cell: Not observed.
(3) Mobility: The present bacterium has polar flagella and accordingly mobility.
(4) Spore: Not formed.
(5) Gram-staining: Negative (6) Acid-fast: Negative

(B) Growth in various media (1) Bouillon-agar plate culture: In 24 hr culture at 30° C., there appears a light yellowish brown and transparent colony having a smooth surface and a dim luster. No pigment is formed.
(2) Bouillon-agar slant culture: Growth is good. The same result as explained in above (1) is obtained.
(3) Bouillon liquid culture: Growth is uniform and good.
(4) Bouillon-gelatin stab culture: In 4 days culture at 30° C., slight growth is seen and there appears liquefaction of the culture medium
(5) Litmuth milk: Change to slightly alkaline

(C) Physiological properties (1) Reduction of nitrate: Negative
(2) Denitrogenating reaction: Negative
(3) MR test: Negative
(4) VP test: Negative
(5) Indole formation: Negative
(6) $H_2S$ formation: Negative
(7) Hydrolysis of starch: Negative
(8) Utilization of citric acid: Utilizes citric acid in both of Koser and Christensen media.
(9) Utilization of inorganic nitrogen sources: Utilizes ammonia but does not utilize nitrates.
(10) Pigment formation: Negative
(11) Urease: Negative
(12) Oxidase: Positive
(13) Catalase: Positive (14) Growth conditions: Optimum pH range is 5 to 8. Optimum temperature range is 30° to 38° C.
(15) Behavior toward oxygen: Aerobic
(16) 0-F test: Oxidative
(17) Formation of acids and gases from saccharides

| Saccharide | Acid formation | Gas formation |
|---|---|---|
| L-arabinose | + | − |
| D-xylose | + | − |
| D-glucose | + | − |
| D-mannose | − | − |
| D-fructose | + | − |
| D-galactose | + | − |
| Maltose | − | − |
| Saccharose | − | − |
| Lactose | − | − |
| Trehalose | − | − |
| D-sorbitol | − | − |
| D-mannitol | − | − |
| Inositol | − | − |
| Glycerine | − | − |
| Starch | − | − |

(D) Other properties (1) In a medium limited in quantity of nitrogen sources, accumulates poly-$\beta$-hydroxybutyric acid esters in cells.
(2) Can not grow by using only DL-arginine and betaine as carbon sources.
(3) Grows at 40° C.
(4) Does not utilize hydrogen as an energy source.

The above bacteriological properties of the novel bacterium of the present invention having an ability of producing an oxidase for N-acetylhexosamine are compared with the classification of "Bergey's Manual of Determinative Bacteriology" (8th edition, 1974). The present bacterium shows negative Gram-staining, is an aerobic sporeless bacillus, has polar flagella and accordingly mobility, and is positive for catalase and oxidase; and accordingly belongs to the genus Pseudomonas and is classified into Section 3 and, because it grows at 41° C., appears to be identical with Pseudomonas lemoignei, however, is entirely different from Pseudomonas lemoignei in liquefaction of gelatin, utilization of saccharides, etc. Based on these facts, the present bacterium has been named as Pseudomonas sp. No. 15-1. Incidentally, the strain Pseudomonas sp. 15-1 was deposited internationally as FERM BP-227 on Dec. 21, 1982, in the Fermentation Research Institute, Agency of Industrial Science and Technology, Japan, in accordance with Budapest Treaty on the International Recognition of the Deposit of Microorganisms for the Purposes of Patent Procedure.

As the medium used for culture of the above bacterial strain, synthetic media as well as natural media can be used so long as they contain sources, nitrogen sources, inorganic matters and other nutrients appropriately. As carbon sources, there can be used glucose, galactose, fructose, xylose, arabinose, etc. and further glycine, mannitol, propionic acid, glycolic acid, lactic acid, etc. As nitrogen sources, there can be used preferably ammonium salts, proteinous digests such as peptone digest, casein digest and the like, and nitrogen-containing organic matters such as yeast extract and the like. As inorganic matters, there can be used salts of sodium, potassium, manganese, magnesium, calcium, cobalt, nickel, iron, copper, zinc and other metals. In the present invention, the yield of N-acetylhexosamine oxidase becomes highest when the strain having an ability of producing an N-acetylhexosamine oxidase is cultured in a medium containing N-acetylhexosamine. Preferable examples of such a culture medium include, for example, a medium of pH 6.5 containing 0.5% of N-acetylglucosamine, 0.4% of yeast extract, 0.15% of polypeptone, 0.5% of glycerine, 0.05% of magnesium sulfate and 0.2% of potassium secondary phosphate. When a culture is conducted in this medium for 20 hr at 30° C. with stirring by air, the produced activity for N-acetylhexosamine oxidase is ten- to fifty-fold compared with when the same culture is made by replacing N-acetylglucosamine with glucose. The culturing temperature usually is in the range of 20° to 40° C., preferably 33° to 38° C. pH at the start of culture usually is in the range of 6 to 8, preferably about 7. By conducting a shaking culture or a submerged stirring culture for 18 to 20 hr under the above conditions, an N-acetylhexosamine oxidase is formed and accumulates in the culture products.

The N-acetylhexosamine oxidase formed above is present usually within bacterial cells. Therefore, the culture products are collected by centrifugation or filtration and then the bacterial cells are destroyed in an appropriate amount of a buffer solution, whereby the enzyme is dissolved and released into the solution. For destruction of the bacterial cells, (a) physical methods using an apparatus such as Dyno mill, French press, ultrasonic wave and the like, (b) chemical methods using chemicals such as Triton X-100, a surface active agent composed mainly of polyethylene glycol mono-p-iso-octylphenol ether, Rohm and Haas Company, Philadelphia, Pa., sodium lauryl sulfate, ethylenediaminetetraacetic acid sodium salt (EDTA) and the like, and (c) enzymatic methods using an enzyme such as lysozyme and the like can be used alone or in combination. The thus obtained solution wherein the bacterial cells are present in destroyed form is freed of nucleic acids in an ordinary manner and then freed of insolubles by filtration or centrifugation to obtain an N-acetylhexosamine oxidase. This N-acetylhexosamine oxidase is purified, if necessary, by an ordinary method for enzyme separation and purification, for example, by single or combination use of (1) a column chromatography by CM-cellulose column, (2) a fractional precipitation method by ammonium sulfate, (3) a column chromatography by CM-Sephadex column, (4) a gel filtration method by Sephadex and (5) any other appropriate method, whereby a purified N-acetylhexosamine oxidase can be obtained.

An example of production of the N-acetylhexosamine oxidase will be explained below.

Pseudomonas sp. No. 15-1 (FERM BP-227) is inoculated into 100 ml of a seed medium of pH 6.5 having a composition of 5 g/l of N-acetylglucosamine, 4 g/l of yeast extract, 1 g/l of potassium phosphate and 0.5 g/l of magnesium sulfate, in a 500 ml flask. Then, culture is conducted for 8 hr at 30° C. The thus obtained seed culture liquid is inoculated into 20 l of an enzyme production medium of pH 6.5 having a composition of 5 g/l of N-acetylglucosamine, 4 g/l of yeast extract, 5 g/l of glycerine, 1.5 g/l of polypeptone, 2 g/l of dipotassium hydrogen-phosphate and 0.5 g/l of magnesium sulfate, in a 30 l jar fermenter. Culture is conducted for 20 hr at 35° C. with stirring (300 rpm) and aeration (20 l/min). Then, the culture liquid is subjected to centrifugation (12,000 rpm) to collect bacterial cells. To 411 g of the bacterial cells collected is added 2 l of 0.05M potassium phosphate buffer solution of pH 7.0 to disperse the bacterial cells thoroughly. Thereto is added 200 ml of 10% aqueous Triton X-100 solution and thorough stirring is applied. Further, thereto is added 2.5 l of 0.05M potassium phosphate buffer solution of pH 7.0, and the mixture was allowed to stand overnight at low temperatures. Then, a saturated protamine sulfate solution of pH 7.5 is added until no more precipitate appeared. The precipitate is removed by centrifugation (2000 rpm) and the supernatant is condensed by the use of a hollow fiber ultrafiltration apparatus. The condensate is dialyzed against 0.05M acetic acid buffer solution using a cellulose tube, then adsorbed in a column (10.5 cm $\phi \times 40$ cm L) packed with CM-cellulose equilibrated with the same buffer solution and finally eluted by KCl eluting solutions having a concentration gradient of 0 to 0.6M KCl.

The active fractions eluted are put together and condensed to 400 ml by the use of a hollow fiber ultrafiltration apparatus. To the condensate, is added ammonium sulfate so that the latter becomes 30% saturation and the insolubles are removed by centrifugation. Further, ammonium sulfate is added so that it becomes 55% saturation and the resulting precipitate is collected by centrifugation and dissolved in 50 ml of 0.05M potassium phosphate buffer solution of pH 6.8 containing 35% saturation ammonium sulfate. The resulting insolubles are removed by centrifugation. The thus obtained solution is equilibrated with the same buffer solution in which the concentration of ammonium sulfate is 35% saturation. Then, the solution is subjected to adsorption in a column (4 cm $\phi \times 15$ cm L) packed with Phenyl Sepharose CL-4B manufactured by Pharmacia Co., Sweden. Elution is conducted by the use of 0.05M potassium phosphate buffer solutions of pH 6.8 having a concentration gradient (0 to 30%) of ethylene glycol and a reverse concentration gradient (20% saturation to 0) of ammonium sulfate. The active fractions eluted are collected and condensed by using an ultrafiltrating membrane. The condensate is dialyzed overnight against 0.1M acetic acid buffer solution of pH 5.25 using a cellulose tube. The dialyzate is subjected to adsorption in a column (3.5 cm $\phi \times 45$ cm L) packed with CM-Sephadex C-50 equilibrated with the same buffer solution. Elution is conducted by the use of eluting solutions having a concentration gradient (0 to 0.5M) of sodium chloride. The active fractions eluted are collected and condensed. The condensate is dialyzed against 0.05M potassium phosphate buffer solution of pH 6.8 containing 0.1M sodium chloride using a cellulose tube. The dialyzate is subjected to gel filtration by the use of a column (2 cm $\phi \times 100$ cm L) packed with Sephadex G-200 equilibrated with the same buffer solution. The first half of the filtrate having a high relative activity is condensed, whereby 21 mg of purified N-acetylhexosamine oxidase is obtained. Yield: 4.1%; Relative activity: 15.5 unit/mg protein.

The thus obtained enzyme has the following physicochemical properties.

(1) Action and specificity for substrate

As shown in the following reaction formula, the present enzyme oxidizes N-acetylhexosamine in the presence of oxygen to form N-acetylhexosaminic acid and hydrogen peroxide. The present enzyme hardly acts or does not at all act on hexose, hexosamine and N-acetylneuraminic acid.

N—acetylhexosamine

N—acetylhexosaminic acid

Incidentally, specific examples of N-acetylhexosamines are shown in Table 1.

TABLE 1

| N—acetylhexosamines | $R_1$ | $R_2$ | $R_3$ | $R_4$ | $R_5$ |
|---|---|---|---|---|---|
| N—acetylglucosamine | —H | —OH | —OH | —H | —NHCOCH$_3$ |
| N—acetylgalactosamine | —OH | —H | —OH | —H | —NHCOCH$_3$ |

TABLE 1-continued

| N—acetylhexosamines | R₁ | R₂ | N—acetylhexosamines R₃ | R₄ | R₅ |
|---|---|---|---|---|---|
| N—acetylmuramic acid | —H | —OH |  | —H | —NHCOCH₃ |
| N,N—diacetylchitobiose | —H |  | —OH | —H | —NHCOCH₃ |
| N—acetylmannosamine | —H | —OH | —OH | —NHCOCH₃ | —H |

(2) Optimum pH and stable pH range

Figure 1:
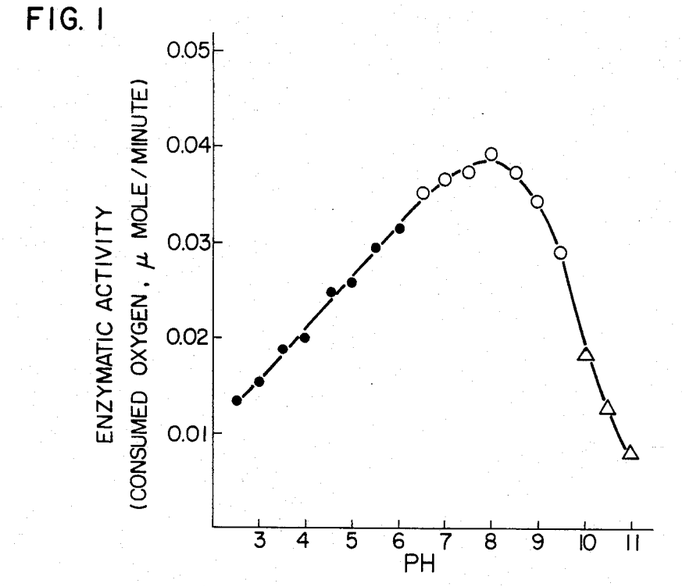
FIG. 1 shows an optimum pH range of an example of the enzyme used in the present invention.
Figure 2:
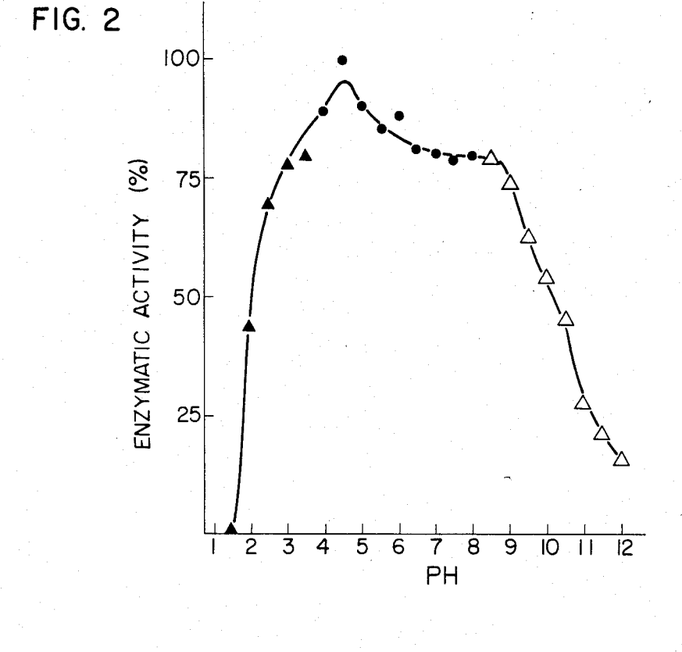
FIG. 2 shows a pH range in which the enzyme is stable.

When a potassium phosphate buffer solution containing 0.1M glycine is used, the optimum pH of the present enzyme is 7.5 to 8.5. As an example, the activity of the present enzyme for N-acetylglucosamine was measured by the use of a citric acid-sodium phosphate buffer solution, a potassium phosphate buffer solution containing 0.1M glycine and a glycine-sodium hydroxide buffer solution and the result obtained is shown in FIG. 1, in which the optimum pH of the present enzyme is 7.5 to 8.5. The measurement was made in the citric acid-sodium phosphate buffer solution, the potassium phosphate buffer solution containing 0.1M glycine and the glycine-sodium hydroxide buffer solution, in accordance with an consumed oxygen method. The pH range in which the present enzyme is stable is 3 to 9 as shown in FIG. 2. This stable pH range is measured by employing a hydrogen peroxide method and by dissolving the present enzyme in 0.1 ml of a citric acid-sodium phosphate buffer solution and a glycine-hydrochloric acid or sodium hydroxide buffer solution, heat-treating the resulting solution for 10 minutes at 45° C. and then measuring the residual activity of the enzyme.

Note: Measurement of enzymatic activity (a) By measuring oxygen consumed

In a closed vessel there are placed 2.9 ml of 0.1M potassium phosphate buffer solution of pH 8.0 containing 0.1M glycine and 0.1 ml of 0.5M N-acetylglucosamine solution. Then, an oxygen electrode manufactured by YSI Company of U.S.A. is inserted therein. While the content of the reaction vessel is being stirred at 37° C., 10 μl of the present enzyme in liquid form is added thereto to start a reaction. The amount of oxygen consumed is measured periodically by the use of an oxygen monitor manufactured by YSI Company. Incidentally, an enzymatic activity of consuming 1 μmol of oxygen per minutes is taken as 1 enzyme unit.

(b) By measuring hydrogen peroxide produced

In 0.1M potassium phosphate buffer solution of pH 6.8, are dissolved 0.005% of 4-aminoantipyrine, 0.02% of N,N-dimethylaniline and peroxidase. To 2.8 ml of the resulting solution in which peroxidase activity is 4 units, are added 0.1 ml of 0.5M N-acetylglucosamine and 0.1 ml of the present enzyme in liquid form to make the total volume 3 ml. The resulting mixture is subjected to reaction for 10 minutes at 37° C. Then, absorption at visible region (550 nm) is measured for the pigment produced, and the amount of hydrogen peroxide produced is calculated by the use of a standard curve.

(c) By measuring N-acetylhexosaminic acid produced

To 2.8 ml of 0.1M potassium phosphate buffer solution of pH 8.0 is added 0.1 ml of 0.5M N-acetylglucosamine. Then, thereto is added 0.1 ml of the present enzyme of liquid form. The resulting mixture is subjected to reaction for 10 minutes at 37° C. An appropriate volume of the reaction mixture is subjected to high performance liquid chromatography [column: TSK-GEL LS-220 manufactured by Toyo Soda; column size: 4 mm φ×250 mm L; mobile phase: 0.03M sodium chloride-0.025M sodium phosphate buffer solution of pH 7.0; temperature: 40° C.; detection: UV 220 nm], for separation of N-acetylglucosaminic acid. By comparing the height of the peak obtained with that of a standard product, N-acetylglucosaminic acid is determined quanitatively.

(3) Temperature range suitable for action

Figure 3:
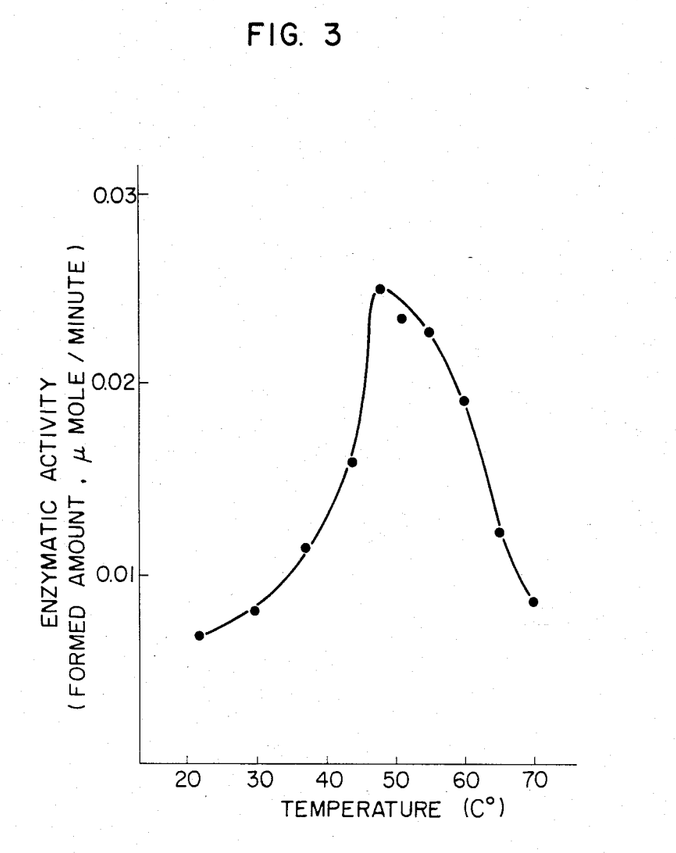
FIG. 3 shows a temperature range suitable for action of the enzyme.

As shown in FIG. 3, a temperature range suitable for action of the present enzyme is 30° to 70° C. according to the result of measurement of the amount of N-acetylglucosaminic acid separated by the use of high performance liquid chromatography. This experiment was conducted by measuring the amount of produced N-acetylglucosaminic acid at each temperature in accordance with the method for quantitatively determining N-acetylhexosaminic acid.

(4) Deactivation conditions such as pH and temperature

Figure 4:
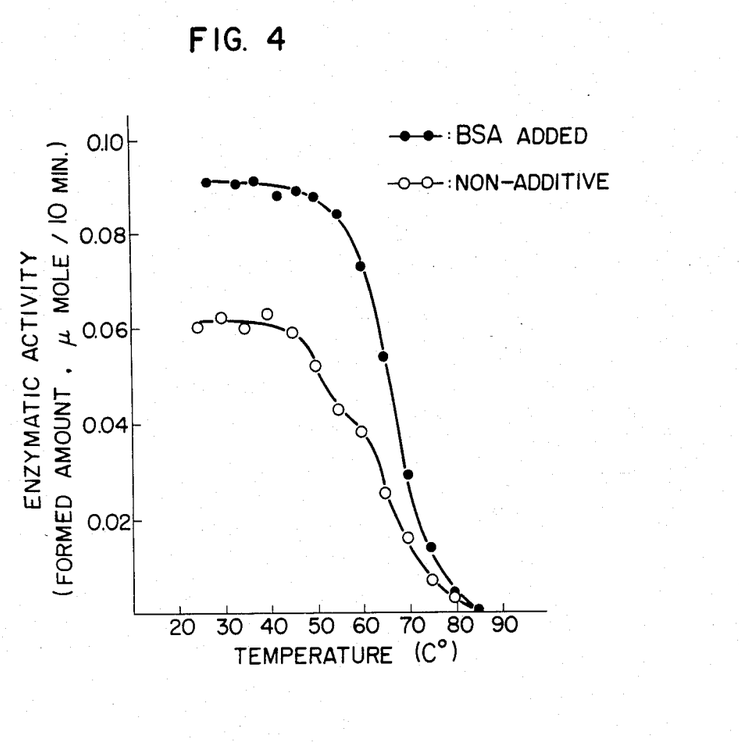
FIG. 4 shows deactivation of the enzyme at each temperature.

As shown in FIG. 4, in 10 minutes heat treatment, deactivation of the present enzyme begins at 45° C. but the present enzyme retains about half of its activity even at 65° C. Further, in 10 minutes heat treatment at 45° C., the present enzyme is stable between pH 3 and pH 9 and loses its activity rapidly at a more acidic region and slowly at a more alkaline region. In this experiment, the hydrogen peroxide method was adopted, and the residual activity of the present enzyme subjected to 10 minutes heat treatment in a potassium phosphate buffer solution of pH 6.8 at each temperature was compared with the residual activity of the same enzyme subjected to the same treatment in a potassium phosphate buffer solution of pH 6.8 containing 1 mg/ml of bovine serum albumin.

(5) Activity inhibition and activity stabilization

The activity of the present enzyme was measured in various solutions each comprising a tris-hydrochloric acid buffer solution of pH 7.5 and 1.8mM metallic ion or inhibitor. The results are shown in Table 2. As is obvious from Table 2, the activity is inhibited greatly by iron (bivalent), mercury and zinc, and considerably by cadmium, lead and nickel.

Meanwhile, as shown in FIG. 4, the activity of the present enzyme is stabilized and moreover slightly enhanced by addition of bovine serum albumin.

TABLE 2

| Inhibitor | Residual activity (%) | Inhibitor | Residual activity (%) |
|---|---|---|---|
| No addition | 100 | KCN | 95 |
| Pb(CH$_3$COO)$_2$ | 42 | FCH$_2$COONa | 107 |
| HgCl$_2$ | 17 | EDTA[1] | 87 |
| AgNO$_3$ | 5 | PCMB[2] | 67 |
| (Phosphate buffer solution) | | ICH$_2$CONH$_2$ | 90 |
| | | o'-Phenanthroline | 81 |
| ZnSO$_4$ | 2 | 8-Hydroxyquinoline | 102 |
| FeSO$_4$ | 15 | α,α'-Dipyridyl | 106 |
| CdBO$_4$ | 52 | SDS[3] | 87 |
| NiSO$_4$ | 64 | | |
| CuSO$_4$ | 74 | | |
| CoSO$_4$ | 75 | | |
| MgSO$_4$ | 86 | | |
| CaCl$_2$ | 91 | | |
| MnSO$_4$ | 84 | | |
| NaN$_3$ | 103 | | |

[1]EDTA: Ethylenediaminetetraacetic acid sodium salt
[2]PCMB: p-Chloromercurybenzoate
[3]SDS: Sodium dodecylsulfate (6) Purification The present enzyme can be separated and purified according to a usual method. For example, purification methods such as the column chromatography by a CM-cellulose column, the fractional precipitation method by ammonium sulfate, the column chromatography by a CM-Sephadex column, the gel filtration method by Sephadex and the like are used alone or in appropriate combinations.

(7) Molecular weight

The present enzyme has a molecular weight of about 140,000 to 150,000 when measured in accordance with the gel filtration method by a Sephadex G-200 column using 0.05M potassium phosphate buffer solution containing 0.1M sodium chloride.

(8) Electrophoresis by a polyacrylamide gel

Figure 5:
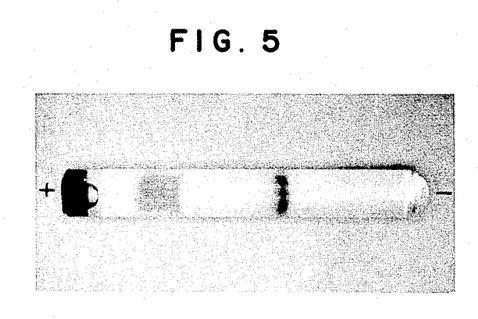
FIG. 5 shows a polyacrylamide disc electrophoresis of the enzyme.

Polyacrylamide disc electrophoresis was conducted by using a gel (pH 4.0) of a polyacrylamide having 7.5% acrylamide concentration in accordance with a usual method. As a result, as shown in FIG. 5, a single band was observed.

(9) Isoelectric point

The isoelectric point of the present enzyme is 8.0 when measured by the polyacrylamide gel isoelectric focusing method.

(10) Analysis of amino acids

The following numbers represent molecule numbers of each amino acid present in one molecule of the present enzyme.

Aspartic acid 133, threonine 83, serine 72, glutamic acid 103, glycine 137, alanine 152, ½ cystine 28, valine 99, methionine 22, isoleucine 44, leucine 120, tyrosine 52, phenylalanine 38, lysine 49, histidine 37, arginine 78, tryptophane 18, proline 83.

As understood from the above, the present enzyme is a novel enzyme unknown to date, in its action and specificity for substrate.

When the N-acetyl hexosamine oxidase is allowed to act upon an N-acetylhexosamine-containing liquid, it is conducted at a pH of 3 to 10 and a temperature of 70° C. or below, preferably at a pH of 5 to 9 and a temperature of 40° to 60° C., usually for about 10 to 20 minutes, whereby a reaction takes place. This pH range can be maintained by the use of an optional buffer solution not inhibiting intended enzymatic reactions. The use of, for example, a potassium phosphate buffer solution, a tris-hydrochloric acid buffer solution, or a citric acid-sodium phosphate buffer solution is preferable. The amount of the N-acetylhexosamine oxidase used is usually 0.2 unit or above.

In the present invention, N-acetylhexosamine is determined quantitatively by either of the following methods.

(a) Determination by measurement of oxygen consumed

In this quantitative determination method, the amount of oxygen consumed is calculated as the amount of oxygen at the start of reaction minus the amount of oxygen at the end of reaction and then, by using a separately prepared calibration line between the amount of oxygen consumed and the amount of N-acetylhexosamine, N-acetylhexosamine in a sample is determined quantitatively. The measurement of the amount of oxygen consumed is conducted by an ordinary method such as, for example, the Warburg's manometric technique, the oxygen electrode method or the like. When the amount of oxygen consumed is measured by the oxygen electrode method, there can be used, for example, the same procedure as described in (3) Measurement of enzymatic activity, (a) By measuring oxygen consumed.

(b) Determination by measurement of hydrogen peroxide formed in enzymatic reaction The amount of hydrogen peroxide formed in enzymatic reaction is determined quantitatively by an ordinary method for quantitative determination of hydrogen peroxide such as, for example, the color development method or the method using a hydrogen peroxide electrode. Then, by using a separately prepared calibration line between the amount of hydrogen peroxide and the amount of N-acetylhexosamine, the amount of N-acetylhexosamine in a sample is determined quantitatively. When hydrogen peroxide is determined by the color development method, there can be used, for example, the same procedure as described in (3) Measurement of enzymatic activity, (b) By measuring hydrogen peroxide produced.

(c) Determination by measurement of N-acetylhexosaminic acid formed in enzymatic reaction N-acetylhexosaminic acid formed in enzymatic reaction is determined quantitatively by an ordinary method such ① as the method by a carboxylic acid analyzer or ② the method wherein N-acetylhexosaminic acid is separated by the high performance liquid chromatography and then its absorbance at an UV region is measured. Then, by using a separately prepared calibration line between the amount of N-acetylhexosaminic acid and the amount of N-acetylhexosamine, N-acetylhexosamine in a sample is determined quantitatively. When N-acetylhexosaminic acid is determined by the above method ②, there can be used, for example, the same procedure described in (3) Measurement of enzymatic activity, (c) By measuring N-acetylhexosaminic acid produced.

The reagent for quantitative determination of N-acetylhexosamine of the present invention is composed of an N-acetylhexosamine oxidase, a buffer solution giving a pH preferable for execution of an intended enzymatic reaction, usually a pH of 3 to 10, preferably a pH of 5 to 9, and further, when a reaction product is determined, as necessary, a color-developing agent or the like.

The N-acetylhexamine oxidase can be in liquid form or in powder form. Its amount per one test sample is usually at least 0.2 unit. Preferable buffer solutions are, for example, a potassium phosphate buffer solution, a tris-hydrochloric acid buffer solution, an acetic acid buffer solution, and a citric acid-sodium phosphate buffer solution. As the color-developing agent used in determination of a reactive product, there are used substances which develop colors by reacting with the reaction product. As the color-developing agent for hydrogen peroxide, there are mentioned, for example, combinations between peroxidase and 4-aminoantipyrine/N,N'-diethylamine, 4-aminoantipyrine/phenol, 4-aminoantipyrine/N,N'-dimethylamine, [2,2'-azinodi(3-ethylbenzothiazoline-6-sulfonate], or (3-methyl-2-benzothiazolinone hydrazone)/N,N'-dimethylaniline. It is preferable that the reagent for quantitative determination of N-acetylhexosamine of the present invention be stored in a dark place of cold temperature, particularly of 5° C. or lower.

According to the present invention, N-acetylhexosamine present in decomposition products of mucopolysaccharides excreted in urine as well as N-acetylhexosamine formed by glucosamine-6-phosphoric acid synthesis enzyme, uridine diphosphate-N-acetylhexosamine epimerase, uridine diphosphate-N-acetylglucosamine transferase, chitinase, lysozyme, etc. can be determined efficiently. This determination can be effectively utilized in inspection of conditions of various diseases.

Hereunder, the present invention will be explained in more detail by way of Examples, however, is in no way restricted to these Examples. The N-acetylhexosamine oxidase used in each Example is same as obtained in the previously described example of N-acetylhexosamine oxidase production.

EXAMPLE 1

Acidic mucopolysaccharides were separated from human urine in accordance with the procedure described in Medical Chemistry Experiments IB, Human Body Constituents II, page 10 (published on Feb. 28, 1972). To 1 mg of the acidic mucopolysaccharides, was added 2 ml of 4N hydrochloric acid. The mixture was subjected to thermal decomposition for 4 hr at 100° C. The reaction mixture was neutralized with 4N sodium hydroxide. Thereto were added 34.0 mg of sodium bicarbonate and 0.4 ml of methanol. The mixture was ice-cooled and then 15.3 mg of acetic anhydride was added. The mixture was allowed to stand for 1 hr in an ice water and then for 30 minutes in an hot water of 50° C. Subsequently, the mixture was adjusted to pH 5.7 by the use of an acetic acid solution and Methyl Red (indicator) and the total volume was made 10 ml.

One milliliter of the thus treated test liquid was placed in an oxygen monitor (manufactured by YSI Company, U.S.A.) which is a vessel for oxygen determination. Thereto was added 2 ml of 0.1M acetic acid buffer solution of pH 5.7. Also, an oxygen electrode was inserted therein. Then, the vessel was sealed. The temperature of the vessel contents were kept at 37° C. with stirring the contents. Thereto was added 1 unit (30 μl) of the N-acetylhexosamine oxidase to start a reaction. From the start of the reaction to its completion, oxygen amount in the vessel was determined with the elapse of time and recorded continuously by a recorder (manufactured by Sekonic Co., Ltd., Japan) connected to the monitor. The oxygen amount in the vessel at the start of reaction minus the oxygen amount in the vessel at the end of reaction was calculated as the oxygen amount consumed for reaction which was 25.7 as a reading on the recording sheet.

Using N-acetylglucosamine standard solutions, oxygen amounts consumed for these solutions were determined in the same manner as described above. In these standard solutions, a relation between N-acetylglucosamine amount and oxygen amount consumed (reading on the recording sheet) is linear and this straight line can be used as a calibration line. From this calibration line, the amount of N-acetylhexosamine in the above mentioned sample was 57 μg and the proportion of N-acetylhexosamine in the acidic mucopolysaccharides was 57%.

EXAMPLE 2

To 1 ml of 0.1M potassium phosphate buffer solution of pH 6.0 was added 0.5 ml of colloidal chitin (concentration: 1 mg/ml). Thereto were added 1 unit (30 μl) of chitobiase (EC 3.2.1.29) derived from *Asperigillus oryzae* and 0.1 ml of a standard chitinase product derived from *Streptomyces griseus* of unknown concentration. The mixture was subjected to reaction for 1 hr at 30° C. to decompose chitin and form N-acetylglucosamine. Then, the mixture was heated for 5 minutes at 100° C. and the reaction was terminated. Thereto was added 0.5 unit (10 μl) of the N-acetylhexosamine oxidase and the mixture was subjected to reaction for 20 minutes at 30° C.

Next, the resulting precipitate was removed by centrifugation and 20 μl of the centrifugate was subjected to separation procedure by the use of a high performance liquid chromatography [column: TSK-GEL LS-220 manufactured by Toyo Soda, column size: 4 mm φ×250 mm L, mobile phase: 0.025M potassium phosphate (pH 7.0)+0.025M KCl, temp.: 45° C., pressure: 25 kg/cm$^2$, range: 0.02]. The eluted N-acetylglucosaminic acid was detected by UV 220 nm. In the above chromatography, the entire progressive status was recorded continuously by a recorder (manufactured by Sekonic Co., Ltd.). N-acetylglucosaminic acid was eluted separately from non-adsorbed substances. The height of the peak of the acid was 23 (reading on recording sheet).

Using N-acetylglucosamine standard solutions, N-acetylglucosaminic acid amounts were measured in the same manner as described above, as peak heights on respective recording sheets. Then, a calibration line was prepared. The amount of N-acetylglucosamine in the above sample formed by chitinase and chitobiase was 48.5 μg.

EXAMPLE 3

To 2.5 ml of 0.1M citric acid/0.2M sodium phosphate buffer solutuon of pH 5.3 containing 0.005% of 4-aminoantipyrine and 0.02% of N,N'-dimethylaniline, was added 1.2 μmol of hexa-n-acetylchitohexaose (hexamer of N-acetylglucosamine). The mixture was kept at 50° C. Then, thereto was added 0.3 ml of human serum and the mixture was subjected to reaction for 1 hr to decompose the substrate. Thereto were added 0.5 unit (50 µl) of N-acetylhexosaminidase prepared from a yeast (*Trichosporon behrendii* IFO 0844), 0.5 unit (50 µl) of N-acetylhexosamine oxidase and 4 unit (10 µl) of peroxidase. The mixture was subjected to reaction for 10 min. The reaction mixture was subjected to colorimetric determination at 550 nm. The difference between the absorbance of this mixture and the absorbance of a reaction mixture obtained from the same procedure except that no human serum was added, was 0.143.

Separately, by using standard N-acetylglucosamine instead of hexa-N-acetylchitohexaose, a calibration line was prepared in the same manner as described above. From this calibration line, the amount of N-acetylglucosamine produced by lysozyme in the serum used as a sample and N-acetylhexosaminidase was found to be 10.5 µg.

EXAMPLE 4

To 1 ml (50 µmol) of a tris-hydrochloric acid buffer solution of pH 7.4, were added 10 µmol of fructose-6-phosphoric acid, 2.6 µmol of acetyl coenzyme A, 12 µmol of L-glutamine and 0.5 unit of glucosamine-6-phosphoric acid acetyltransferase (EC 2.3.1.4) obtained from red bread mould, in an oxygen monitor (manufactured by YSI Co., U.S.A.) which is an oxygen determination vessel. Incubation was conducted at 37° C. Then, thereto was added 0.2 ml (protein amount: 2.0 mg) of an extract obtained by subjecting rat liver to extraction by physiological saline solution containing 1 mmol of EDTA. The mixture was subjected to reaction for 60 minutes at 37° C., whereby glucosamine-6-phosphoric acid was formed from fructose-6-phosphoric acid and L-glutamine and at the same time, by transfer of acetyl group to the amino group of glucosamine-6-phosphoric acid, N-acetylglucosamine-6-phosphoric acid was formed. After 2 minutes heating at 100° C., the reaction was terminated. After cooling, in order to remove phosphoric acid at 6-position, thereto was added a solution of 15 unit of alkaliphosphatase (EC 3.1.3.1) (obtained from *Echerichia coli*) dissolved in 1.5 ml of 0.1M tris-hydrochloric acid buffer solution of pH 8.0 containing 1 mg/1 ml of BSA (bovine serum albumi). Further, 0.1 ml of 0.1M magnesium chloride was added. Incubation was made for 10 minutes at 37° C.

In order to determine the formed N-acetylglucosamine, an oxygen electrode was inserted into the vessel and then the vessel was sealed. With stirring the vessel contents at 37° C., 1.0 unit (30 µl) of N-acetylhexosamine oxidase was added. The amount of oxygen consumed was determined by the oxygen monitor. The entire progressive status of this determination was recorded by a recorder (manufactured by Sekonic Co., Ltd.) which was connected to the oxygen monitor. The oxygen amount in the vessel at the start of reaction minus the oxygen amount in the vessel at the end of reaction was taken as the amount of oxygen consumed. As a result, the amount of oxygen consumed was 8.4 (reading on recording sheet).

A calibration line was prepared in the same determination procedure as above except that standard N-acetylglucosamine was used in place of fructose-6-phosphoric acid. By using this calibration line, the amount of N-acetylglucosamine present in the sample and formed by an enzyme system (glucosamine-6-phosphoric acid synthesis enzyme/glucosamine-6-phosphoric acid acetyltransferase/alkalinephophatase) was found to be 0.07 µmol.

EXAMPLE 5

To 1 ml of 0.1M tris-hydrochloric acid buffer solution of pH 7.5 were added 1 µmol of uridine diphosphate-N-acetylglucosamine and 40 µmol of magnesium sulfate. Incubation was conducted at 37° C. Thereto was added 0.2 ml (protein amount: 2 mg) of a crude enzyme liquid obtained from extracts of a living liver (Biochem. Biophys. Acta Vol. 252, 1971, p. 357). Reaction was conducted for 30 min to form N-acetylmannosamine. The reaction mixture was heated for 2 minutes at 100° C. Thereafter, the mixture was freed from the precipitate, then passed through a column packed with 2 ml of an ion exchange resin of Dowex-1 acetic acid type, and washed with water. The liquid obtained was adjusted to 5 ml in total. Of this volume, 2.5 ml was placed in an oxygen monitor which is an oxygen determination vessel. Thereto was added 0.5 ml of 0.2M tris-hydrochloric acid buffer solution containing 0.2 mole of glycine. The mixture was kept at 37° C. for 10 min. Then, an oxygen electrode was inserted into the vessel and the vessel was sealed. With stirring the contents at 37° C., 9 unit (50 µl) of N-acetylhexosamine oxidase was added. The amount of oxygen consumed was determined in the same manner as in Examples 1 and 4. As a result, an oxygen absorption of 8.0 (reading on recording sheet) was detected. By using a calibration line obtained by subjecting standard N-acetylmannosamine solutions to the same reaction procedure as above, the amount of N-acetylmannosamine present in the sample and formed by uridine diphosphate-N-acetylglucosamine-2'-epimerase was found to be 0.16 µmol.

EXAMPLE 6

| | |
|---|---|
| 0.2 M tris-HCL buffer solution of pH 8.0 | 1.5 ml |
| BSA physiological saline solution 3 mg/ml | 1.0 ml |
| N—acetylglucosamine 2.5 mM | 0 to 100 ml |

The above mixture was placed in an oxygen monitor of YSI Co. which is a vessel for determination of absorbed oxygen. Water was added to obtain a total volume of 3 ml. The contents were kept at 37° C. with stirring. An oxygen electrode was inserted thereto and the vessel was sealed With stirring the contents, 20 µl of N-acetylhexosamine oxidase (50 unit/ml) was added. The oxygen amount in the vessel was recorded continuously during the entire reaction period by a recorder connected to the oxygen monitor. The amount of oxygen consumed was obtained as the oxygen amount at the start of reaction minus the oxygen amount at the end of reaction. As a result, a proportional relationship was confirmed between the amount of N-acetylglucosamine and the amount of oxygen consumed.

EXAMPLE 7

| | |
|---|---|
| BSA physiological saline solution 3 mg/ml | 1.0 ml |
| 4-Aminoantipyrine 0.3 w/v % | 50 μl |
| N,N'—dimethylaniline 0.2 w/v % | 0.3 ml |
| 0.2 M potassium phosphate buffer solution of pH 6.8 | 1.5 ml |
| Peroxidase 400 unit/ml | 10 μl |
| N—acetylgalactosamine 2.5 mM | 0 to 100 μl |
| Distilled water | to obtain a total volume of 2.96 ml |

To the above mixture, was added 20 μl of N-acetylhexosamine oxidase (50 unit/ml). Reaction was conducted for 10 minutes at 37° C. The pigment which developed a color was determined by a colorimetric determination at 550 nm. As a result, a proportional relationship was confirmed between the amount of N-acetylgalactosamine added and the absorbance obtained.

EXAMPLE 8

| | |
|---|---|
| Bovine serum albumine | 100 mg |
| 4-Aminoantipyrine | 5 mg |
| Potassium primary phosphate | 1.36 g |
| Potassium secondary phosphate | 1.74 g |
| Peroxidase | 132 unit |
| N—acetylhexosamine oxidase | 50 unit |
| Glycine | 2.25 g |
| Distilled water | 50 ml |

The above solution was frozen at −40° to −50° C., and then dried for 20 hr in vacuum to obtain an analytical kit (A). As an accompanying liquid for the kit (A), 10 ml of 0.2 w/v % aqueous N,N'-dimethylaniline solution (B) was prepared. In actual use of this combination, a total volume of the solution (B) is added to the analytical kit (A) and then distilled water is added to the mixture to obtain a final volume of 80 ml. The resulting solution is used in a volume of 2.4 ml, relative to 0.6 ml of a test sample.

What is claimed is:

1. A method for quantitative determination of N-acetylhexosamine which comprises (a) allowing an N-acetylhexosamine oxidase to act upon an N-acetylhexosamine-containing liquid in the presence of oxygen and then (b) determining the amount of oxygen consumed in the oxidation reaction or the amount of hydrogen peroxide or N-acetylhexosaminic acid formed in the oxidation reaction, the N-acetylhexosamine being selected from the group consisting of N-acetylglycosamine, N-acetylgalactosamine, N-acetylmuramic acid, N,N-diacetylchitobiose and N-acetylmannosamine.

2. The method of claim 1 wherein said N-acetylhexosamine oxidase is obtained by culturing the bacterium Pseudomonas sp. No. 15-1 (Form BP-227)

3. A reagent for quantitative determination of N-acetylhexosamine comprising an N-acetylhexosamine oxidase, in a buffer solution having a pH of 3 to 10 the N-acetylhexosamine being selected from the group consisting of N-acetylglycosamine, N-acetylgalactosamine, N-acetylmuramic acid, N,N-diacetylchitobiose and N-acetylmannosamine.

4. The reagent of claim 3 wherein said N-acetylhexosamine oxidase is obtained by culturing the bacterium Pseuodomonas sp. No. 15-1 (Form BP-227).

* * * * *

UNITED STATES PATENT AND TRADEMARK OFFICE
CERTIFICATE OF CORRECTION

PATENT NO. : 4,634,663

DATED : January 6, 1987

INVENTOR(S) : Tatsuo Horiuchi

It is certified that error appears in the above-identified patent and that said Letters Patent is hereby corrected as shown below:

Claim 2, line 3, "(Form BP-227)" should read — (Ferm BP-227) —.

Claim 4, line 3, "(Form BP-227)" should read — (Ferm BP-227) —.

Signed and Sealed this

Thirty-first Day of March, 1987

Attest:

DONALD J. QUIGG

*Attesting Officer*  *Commissioner of Patents and Trademarks*